United States Patent [19]

Hofer et al.

[11] 4,032,634

[45] June 28, 1977

[54] O,O-DIALKYL-O-(1-PHENYL-2-CARBALKOXYVINYL)-THIONOPHOSPHORIC ACID ESTERS AND INSECTICIDAL AND ACARICIDAL COMPOSITIONS AND METHOD OF USE THEREOF

[75] Inventors: Wolfgang Hofer; Fritz Maurer; Hans-Jochem Riebel; Rolf Schröder, all of Wuppertal; Paul Uhrhan, Cologne; Bernhard Homeyer, Leverkusen; Wolfgang Behrenz, Overath-Steinenbrueck; Ingeborg Hammann, Cologne, all of Germany

[73] Assignee: Bayer Aktiengesellschaft, Leverkusen, Germany

[22] Filed: Aug. 11, 1976

[21] Appl. No.: 713,738

[30] Foreign Application Priority Data

Aug. 20, 1975 Germany .......................... 2537047

[52] U.S. Cl. ........................... 424/212; 424/210; 260/940; 260/941
[51] Int. Cl.² .................... A01N 9/36; C07F 9/165; C07F 9/18
[58] Field of Search ........... 260/940, 941; 424/210, 424/212

[56] References Cited

UNITED STATES PATENTS 2,894,018  7/1959  Lorenz ........................... 260/941

OTHER PUBLICATIONS

Derwent Japanese, vol. 1, No. 47 (1962) 18736/62.

*Primary Examiner*—Richard L. Raymond
*Attorney, Agent, or Firm*—Burgess, Dinklage & Sprung

[57] ABSTRACT

O,O-Dialkyl-O-(1-phenyl-2-carbalkoxyvinyl)-thionophosphoric acid esters of the formula

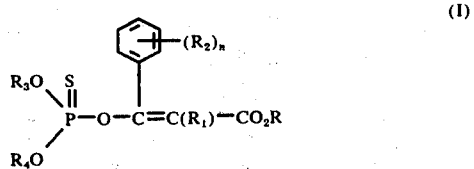

in which
R, $R_3$ and $R_4$ each independently is alkyl with 1 to 6 carbon atoms,
$R_1$ is hydrogen or methyl,
$R_2$ is alkyl, alkoxy or alkylthio each with 1 to 4 carbon atoms, cyano, halogen or phenyl, and
$n$ is 1, 2, 3, 4 or 5,
which possess insecticidal and acaricidal properties.

10 Claims, No Drawings

O,O-DIALKYL-O-(1-PHENYL-2-CARBALKOX-YVINYL)-THIONOPHOSPHORIC ACID ESTERS AND INSECTICIDAL AND ACARICIDAL COMPOSITIONS AND METHOD OF USE THEREOF

The present invention relates to and has for its objects the provision of particular new O,O-dialkyl-O-(1-phenyl-2-carbalkoxyvinyl)-thionophosphoric acid esters which possess insectcidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from Canadian Pat. No. 728,163, published Japanese Pat. No. 18,736/62 and U.S. Pat. No. 3,102,842 that vinyl(thiono)phosphoric acid esters, for example O,O-diethyl-O-(43 1-phenyl-2-carbethoxyvinyl)-(Compound A) and O,O-dimethyl-O-[1-(2,4,5-trichlorophenyl)-2-chlorovinyl]-phosphoric acid ester (Compound B) and O,O-dimethyl-O-[1-(4-nitrophenyl)-2-carbethoxyvinyl]-thionophosphoric acid ester (Compound C), possess insecticidal and acaricidal properties.

The present invention provides as new compounds the vinyl-thionophosphoric acid esters of the general formula

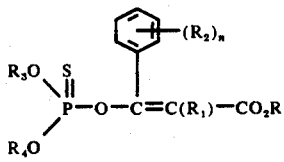

in which
R, $R_3$ and $R_4$ each independently is alkyl with 1 to 6 carbon atoms,
$R_1$ is hydrogen or methyl,
$R_2$ is alkyl, alkoxy or alkylthio each with 1 to 4 carbon atoms, cyano, halogen or phenyl, and
$n$ is 1, 2, 3, 4 or 5, Preferably, $R_3$ and $R_4$, which may be identical or different, each represent straight-chain or branched alkyl with 1 to 4 carbon atoms, R represents straight-chain or branched alkyl with 1 to 3 carbon atoms, $R_2$ represents cyano, phenyl, chlorine, fluorine, bromine, iodine, methoxy, ethoxy, methylthio, ethylthio, methyl or ethyl, and $n$ is 1, 2 or 3.

The general formula (I) includes the corresponding cis- and trans-isomers of the structure (II) and (III) and the mixtures of these components:

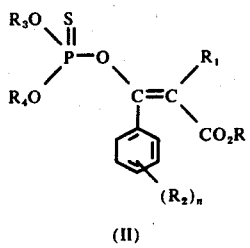 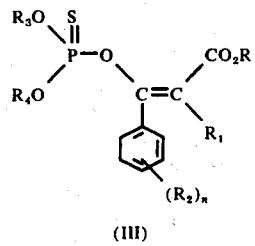

Surprisingly, the vinylthionophosphoric acid esters according to the invention exhibit a better insecticidal and acaricidal action than the previously known vinyl(thiono)phosphoric acid esters of analogous structure and of the same type of action. The compounds according to the present invention thus represent a genuine enrichment of the art.

The present invention provides a process for the preparation of a vinylthionophosphoric acid ester of the formula (I), in which an O,O-dialkylthionophosphoric acid diester halide of the general formula

in which
Hal represents halogen, preferably chlorine, is reacted with a benzoylacetic acid alkyl ester derivative of the formula (V), or its enol form (Va),

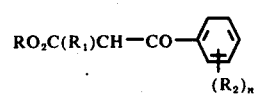 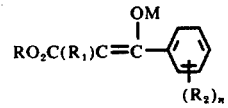

in which formula
M represents hydrogen or one equivalent of an alkali metal, alkaline earth metal or ammonium,
if appropriate in the presence of an acid acceptor and, if appropriate, in the presence of a solvent or diluent.

If, for example, O-ethyl-O-iso-propyl-thionophosphoric acid diester chloride and 2,4,5-trichlorobenzoylacetic acid n-propyl ester are used as starting materials, the course of the reaction can be represented by the following equation:

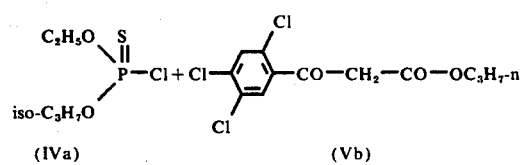

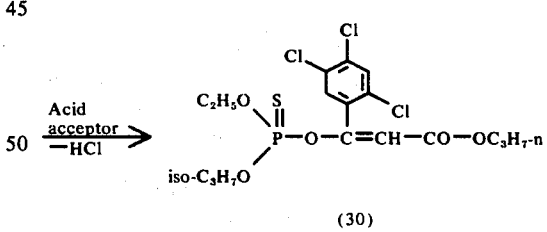

The O,O-dialkylthionophosphoric acid diester halides (IV) required as starting materials are known and can be prepared in accordance with customary processes.

The following may be mentioned as examples of these halides: O,O-dimethyl-, O,O-diethyl-, O,O-di-n-propyl-, O,O-di-isopropyl-, O,O-di-n-butyl-, O,O-di-isobutyl-, O,O-di-sec.-butyl-, O,O-di-tert.-butyl-, O-ethyl-O-n-propyl-, O-ethyl-O-isopropyl-, O-ethyl-O-n-butyl-, O-ethyl-O-isobutyl-, O-methyl-O-ethyl- and O-methyl-O-n-propyl-thionophosphoric acid diester chloride.

Benzoylacetic acid alkyl ester derivatives (V) and (Va) which are also to be used as starting materials have been described and can be prepared in accordance with processes known from the literature (see German published specification DOS No. 2,343,974 and U.S. Pat. Nos. 2,407,942 and 2,367,632), whereas the corresponding α-benzoylpropionic acid esters may be obtained according to customary methods from the sodium salts of the benzoylacetic acid alkyl esters by methylation.

The following may be mentioned as specific examples of these esters: 4-cyano-, 4-phenyl-, 4-chloro-, 4-bromo-, 4-fluoro-, 4-iodo-, 4-ethylthio-, 4-methylthio-, 4-methoxy-, 4-ethoxy-, 4-methyl-, 4-ethyl-, 2-chloro-, 2-bromo-, 2-iodo-, 2-fluoro-, 2-methyl-, 2-ethyl-, 2-methoxy-, 2-ethoxy-, 2-methylthio-, 2-ethylthio-, 2-cyano-, 2,4-dichloro, 2,4-dibromo-, 2,4-difluoro-, 2,4-diiodo-, 2,4-dimethyl-, 2,4-diethyl-, 2,5-dimethyl-, 2,5-diethyl-, 2,4,5-trichloro-, 2,4,5-tribromo- and 2,4,5-triiodo-benzoylacetic acid methyl esters, ethyl esters, n-propyl esters and isopropyl esters, as well as α-[4-cyano-, 4-phenyl-, 4-chloro-, 4-bromo-, 4-fluoro-, 4-iodo-, 4-ethylthio, 4-methylthio-, 4-methoxy-, 4-ethoxy-, 4-methyl-, 4-ethyl-, 2-chloro-, 2-bromo-, 2-iodo-, 2-fluoro-, 2-methyl-, 2-ethyl-, 2-methoxy-, 2-ethoxy-, 2-methylthio-, 2-ethylthio-, 2-cyano-, 2,4-dichloro-, 2,4-dibromo-, 2,4-difluoro-, 2,4-diiodo-, 2,4-dimethyl-, 2,4-diethyl, 2,5-dimethyl-, 2,5-diethyl-, 2,4,5-trichloro-, 2,4,5-tribromo- and 2,4,5-triiodo-benzoyl]-propionic acid methyl esters, ethyl esters, n-propyl esters and isopropyl esters.

The process for the preparation of the compounds according to the invention is preferably carried out in the presence of suitable solvents and diluents. Practically all inert organic solvents can be used for this purpose, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate, ethylate and tert.-butylate, have proved particularly suitable, as have aliphatic, aromatic and heterocyclic amines, for example triethylamine, trimethylamine, dimethylaniline, dimethylbenzylamine and pyridine.

The reaction temperature can be varied within a fairly wide range. In general, the reaction is carried out at between 0° and 120° C, preferably at from 40° to 70° C.

In general, the reaction is allowed to take place under normal pressure.

To carry out the process, the phosphoric acid ester component (IV) and the benzoylacetic acid ester derivative (V) or (Va) are preferably employed in equimolar amounts. An excess of one or other component produces no significant advantages. In most cases, the reaction is carried out in the presence of a solvent and in the presence of an acid acceptor. After completion of the reaction at the stated temperatures, an organic solvent, for example toluene, is added to the solution and the organic phase is worked up in the usual manner by washing, drying and distilling off the solvent.

The present compounds are obtained in the form of oils which in part cannot be distilled without decomposition but are freed from the last volatile constituents by so-called "slight distillation", that is to say by prolonged heating under reduced pressure to moderately elevated temperatures, and are purified in this way. They are characterized by the refractive index.

As already mentioned, the vinylthionophosphoric acid esters according to the invention are distinguished by an excellent insecticidal and acaricidal activity. They are active against plant pests, pests harmful to health and pests of stored products and combine a low phytotoxicity and mammalian toxicity with a good action against both sucking and biting insects and against mites.

For this reason, the compounds according to the invention can be employed successfully as pesticides in plant protection as well as in the hygiene field and in the field of protection of stored products.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (Lepidoptera) such as the diamond-back moth (*Plutella maculipennis*), the gypsy moth (*Lymantria dispar*), the brown-tail moth (*Euproctis chrysorrhoea*) and the tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), but also species living in the soil, for example wireworms (*Agriotes* spec.) and larvae of the cockchafer (*Melolontha melolontha*); cockroaches, such as the German cockroach (*Blattella germanica*); American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta;* further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aëdes aegypti*), the northern house mosquito (*Culex pipiens*) and the malaria mosquito (*Anopheles stephensi*).

With mites (Acarina) there are classed, in particular, the spider mites (Tetranychidae) such as the two-spotted spider mite (*Tetranychus urticae*) and the European red mite (*Paratetranychus pilosus* = *Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the process products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally effective amount, of the particular active compound of the invention alone or together with a carrier vehicle as noted above. The instant formulations or compositions are applied in the usual manner, for instance by spraying, atomizing, vaporizing, scattering, dusting watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is hereinafter quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all test insects had been killed and was 0% if exactly as many test insects were still alive as in the case of the untreated control.

The active compounds, amounts used and results can be seen from the table which follows:

Table 1

(*Phorbia antiqua* grubs in the soil)

| Active compound | | Degree of destruction in % at an active compound concentration of 5 ppm |
|---|---|---|
| $NO_2\text{-}\langle\rangle\text{-}C(OP(S)(OCH_3)_2)=CH\text{-}CO\text{-}OC_2H_5$ (known) | (C) | 0 |
| $Cl\text{-}\langle\rangle\text{-}C(OP(S)(OC_2H_5)_2)=CHC(O)\text{-}OCH_3$ | (18) | 100 |
| $Cl\text{-}\langle\rangle\text{-}C(OP(S)(OC_2H_5)(OC_3H_7\text{-}n))=CHC(O)\text{-}OCH_3$ | (19) | 100 |
| $Cl\text{-}\langle\rangle(Cl)\text{-}C(OP(S)(OC_2H_5)_2)=CHC(O)\text{-}OC_2H_5$ | (20) | 100 |
| $Cl\text{-}\langle\rangle\text{-}C(OP(S)(OC_2H_5)_2)=CHC(O)\text{-}OC_2H_5$ | (23) | 100 |
| $F\text{-}\langle\rangle\text{-}C(OP(S)(OC_2H_5)_2)=CH\text{-}CO\text{-}OCH_3$ | (15) | 100 |
| $Cl_3\text{-}\langle\rangle\text{-}C(OP(S)(OC_2H_5)_2)=CH\text{-}CO\text{-}OC_2H_5$ | (16) | 100 |
| $(CH_3)_2\text{-}\langle\rangle\text{-}C(OP(S)(OC_2H_5)_2)=CH\text{-}CO\text{-}OC_2H_5$ | (1) | 100 |
| $Cl_2\text{-}\langle\rangle\text{-}C(OP(S)(OC_2H_5)_2)=CH\text{-}CO\text{-}OC_2H_5$ | (17) | 100 |
| $CH_3O\text{-}\langle\rangle\text{-}C(OP(S)(OC_2H_5)_2)=CH\text{-}CO\text{-}OC_2H_5$ | (2) | 100 |

Table 1-continued (*Phorbia antiqua* grubs in the soil)

| Active compound | | Degree of destruction in % at an active compound concentration of 5 ppm |
|---|---|---|
| CH₃O−⟨⟩−C(=CH−CO−OC₂H₅)−O−P(=S)(OC₂H₅)(OC₃H₇-n) | (30) | 100 |
| Cl,Cl,Cl-trichlorophenyl−C(=CH−CO−OC₂H₅)−O−P(=S)(OC₂H₅)₂ | (13) | 100 |
| Br−⟨⟩−C(=CH−CO−OC₂H₅)−O−P(=S)(OC₂H₅)₂ | (26) | 100 |

EXAMPLE 2

Test insect: *Tenebrio molitor* larvae in the soil
Solvent: 3 parts by weight of acetone
Emulsifier: 1 part by weight of alkylaryl polyglycol ether To produce a suitable preparation of active compound 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is hereinafter quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all test insects had been killed and was 0% if exactly as many test insects were still alive as in the case of the untreated control.

The active compounds, amounts used and results can be seen from the table which follows:

Table 2

(*Tenebrio molitor* larvae in the soil)

| Active compound | | Degree of destruction in % at an active compound concentration of 5 ppm |
|---|---|---|
| NO₂−⟨⟩−C(=CH−CO−OC₂H₅)−O−P(=O)(OCH₃)₂ (known) | (C) | 0 |
| Cl−⟨⟩−C(=CHC−OCH₃, O)−O−P(=S)(OC₂H₅)₂ | (18) | 100 |
| Cl−⟨⟩−C(=CHC−OCH₃, O)−O−P(=S)(OC₂H₅)(OC₃H₇-n) | (19) | 100 |
| F−⟨⟩−C(CH−CO−OCH₃)−O−P(=S)(OC₂H₅)(OC₂H₅) | (15) | 100 |

EXAMPLE 3

LT₁₀₀ test for Diptera
Test insects: *Musca domestica*
Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was continuously observed. The time which was necessary for 100% destruction was determined.

The active compounds, the concentrations of the activity compounds and the times at which there was 100% destruction can be seen from the following table:

Table 3

(LT$_{100}$ test for *Diptera/Musca domestica*)

| Active compound | | Active compound concentration in the solution in % | LT$_{100}$ in minutes (') or hours (hrs) |
|---|---|---|---|
| NO$_2$–C$_6$H$_4$–C(O–P(S)(OCH$_3$)$_2$)=CH–CO–OC$_2$H$_5$ (known) | (C) | 0.2 | 4 hrs = 60% |
| Cl–C$_6$H$_4$–C(O–P(S)(OC$_2$H$_5$)$_2$)=CH–C(O)–OCH$_3$ | (18) | 0.2<br>0.02 | 70'<br>160' |
| Cl–C$_6$H$_4$–C(O–P(S)(OC$_2$H$_5$)(OC$_3$H$_7$-n))=CH–C(O)–OCH$_3$ | (19) | 0.2<br>0.02 | 130'<br>6 hrs |
| 2,4-Cl$_2$–C$_6$H$_3$–C(O–P(S)(OC$_2$H$_5$)$_2$)=CH–C(O)–OC$_2$H$_5$ | (20) | 0.2<br>0.02 | 75'<br>165' |
| F–C$_6$H$_4$–C(O–P(S)(OC$_2$H$_5$)$_2$)=CH–CO–OCH$_3$ | (15) | 0.2<br>0.02 | 40'<br>60' |
| 2,3-(CH$_3$)$_2$–C$_6$H$_3$–C(O–P(S)(OC$_2$H$_5$)$_2$)=CH–CO–OC$_2$H$_5$ | (1) | 0.2<br>0.02 | 75'<br>210' |
| 2,5-Cl$_2$–C$_6$H$_3$–C(O–P(S)(OC$_2$H$_5$)$_2$)=CH–CO–OC$_2$H$_5$ | (17) | 0.2<br>0.02 | 105'<br>6 hrs |
| 2,4,5-Cl$_3$–C$_6$H$_2$–C(O–P(S)(OC$_2$H$_5$)$_2$)=CH–CO–OC$_2$H$_5$ | (13) | 0.2<br>0.02 | 130'<br>6 hrs |
| Br–C$_6$H$_4$–C(O–P(S)(OC$_2$H$_5$)$_2$)=CH–CO–OC$_2$H$_5$ | (26) | 0.2<br>0.02 | 40'<br>80' |
| CH$_3$S–C$_6$H$_4$–C(O–P(S)(OC$_2$H$_5$)$_2$)=CH–CO–OC$_2$H$_5$ | (14) | 0.2<br>0.02 | 110'<br>60 hrs = 90% |

EXAMPLE 4

Test insects: *Sitophilus granarius*
Solvent: Acetone 2 parts by weight of the active compound were taken up in 1,000 parts by volume of the solvent. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per $m^2$ of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% denotes that all the test insects have been killed; 0% denotes that no test insects have been killed.

The concentrations of the active compounds, the test insects and the results can be seen from the following table:

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 $cm^3$ of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction

Table 4

| Active compound | (*Sitophilus granarius*) | Active compound concentration in the solution in % | Degree of destruction in % |
|---|---|---|---|
| $NO_2$–⟨phenyl⟩–C(O–P(S)(OCH_3)_2)=CH–CO–OC_2H_5 | (C) | 0.2 | 0 |
| (known) | | | |
| Cl–⟨phenyl⟩–C(O–P(S)(OC_2H_5)_2)=CHC(O)–OCH_3 | (18) | 0.2 / 0.02 | 100 / 100 |
| Cl–⟨phenyl⟩–C(O–P(S)(OC_2H_5)(OC_3H_7-n))=CHC(O)–OCH_3 | (19) | 0.2 / 0.02 | 100 / 100 |
| Cl–⟨phenyl, Cl⟩–C(O–P(S)(OC_2H_5)_2)=CHC(O)–OC_2H_5 | (20) | 0.2 / 0.02 | 100 / 100 |
| Cl–⟨phenyl⟩–C(O–P(S)(OC_2H_5)_2)=CHC(O)–OC_2H_5 | (23) | 0.2 / 0.02 | 100 / 100 |
| F–⟨phenyl⟩–C(O–P(S)(OC_2H_5)_2)=CH–CO–OCH_3 | (15) | 0.2 / 0.02 / 0.002 | 100 / 100 / 40 |
| $CH_3O$–⟨phenyl⟩–C(O–P(S)(OC_2H_5)_2)=CH–CO–OC_2H_5 | (2) | 0.2 / 0.02 | 100 / 100 |
| Br–⟨phenyl⟩–C(O–P(S)(OC_2H_5)_2)=CH–CO–OC_2H_5 | (26) | 0.2 / 0.02 | 100 / 100 |

EXAMPLE 5

Drosophila test was determined in %. 100% means that all the flies were killed; 0% means that no flies were killed.

The active compounds, the concentrations of the active compounds, the evaluation times and the results can be seen from the following table:

Table 5

| Active compound | (Drosophila test) | Active compound concentration in % | Degree of destruction in % after 1 day |
|---|---|---|---|
| $NO_2-\underset{}{\bigcirc}-\underset{\underset{C=CH-CO-OC_2H_5}{|}}{\overset{\overset{S}{\|}}{O-P(OCH_3)_2}}$ (known) | (C) | 0.01<br>0.001 | 100<br>0 |
| $\underset{}{\bigcirc}-\underset{\underset{O-P(OC_2H_5)_2}{\|}}{\overset{\overset{CH-CO-OC_2H_5}{\|}}{C}}$ (known) | (A) | 0.01<br>0.001 | 90<br>0 |
| $F-\underset{}{\bigcirc}-\underset{\underset{O-P\underset{OC_2H_5}{\overset{S}{\|}}OC_2H_5}{\|}}{\overset{\overset{CH-CO-OCH_3}{\|}}{C}}$ | (15) | (15)<br>0.01<br>0.001 | 100<br>100 |
| $Cl-\underset{}{\bigcirc}-\underset{\underset{O-P(OC_2H_5)_2}{\|}\atop S}{\overset{}{C=CH\overset{O}{\overset{\|}{C}}-OCH_3}}$ | (18) | (18)<br>0.01<br>0.001 | 100<br>100 |
| $Cl-\underset{}{\bigcirc}-\underset{\underset{O-P(OC_2H_5)_2}{\|}\atop S}{\overset{}{C=CH\overset{O}{\overset{\|}{C}}-OC_2H_5}}$ | (23) | 0.01<br>0.001 | 100<br>100 |
| $Cl-\underset{\underset{Cl}{}}{\bigcirc}-\underset{\underset{O-P\underset{S\ OC_2H_5}{\overset{OC_2H_5}{}}}{\|}}{\overset{}{C=CH\overset{O}{\overset{\|}{C}}-OC_2H_5}}$ | (20) | 0.01<br>0.001 | 100<br>100 |
| $Br-\underset{}{\bigcirc}-\underset{\underset{C=CH-CO-OC_2H_5}{|}}{\overset{\overset{S}{\|}}{O-P(OC_2H_5)_2}}$ | (26) | 0.01<br>0.001 | 100<br>100 |
| $CH_3S-\underset{}{\bigcirc}-\underset{\underset{C=CH-CO-OC_2H_5}{|}}{\overset{\overset{S}{\|}}{O-P(OC_2H_5)_2}}$ | (14) | 0.01<br>0.001 | 100<br>99 |
| $CH_3O-\underset{}{\bigcirc}-\underset{\underset{C=CH-CO-OC_2H_5}{|}}{\overset{\overset{S}{\|}}{O-P(OC_2H_5)_2}}$ | (2) | 0.01<br>0.001 | 100<br>100 |
| $CH_3-\underset{\underset{CH_3}{}}{\bigcirc}-\underset{\underset{CH-CO-OC_2H_5}{}}{\overset{\overset{S\ \ OC_2H_5}{\overset{\|/}{P}}}{\overset{\|}{O-P\diagdown OC_2H_5}}\atop C}$ | (1) | 0.01<br>0.001 | 100<br>100 |
| $NC-\underset{}{\bigcirc}-\underset{\underset{O-P(OC_2H_5)_2}{\|}}{\overset{\overset{C(CH_3)CO-OCH_3}{\|}\atop \overset{S}{\|}}{C}}$ | (4) | 0.01<br>0.001 | 100<br>95 |
| $\underset{}{\bigcirc}-\underset{}{\bigcirc}-\underset{\underset{O-P(OC_2H_5)_2}{\|}}{\overset{\overset{C(CH_3)CO-OCH_3}{\|}\atop \overset{S}{\|}}{C}}$ | (5) | 0.01<br>0.001 | 100<br>95 |

Table 5-continued (Drosophila test)

| Active compound | | Active compound concentration in % | Degree of destruction in % after 1 day |
|---|---|---|---|
| 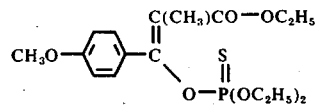 | (7) | 0.01<br>0.001 | 100<br>99 |

EXAMPLE 6

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (Brassica oleracea) which had been heavily infested with peach aphids (Myzus persicae) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 6

(Myzus test)

| Active compound | | Active compound concentration in % | Degree of destruction in % after 1 day |
|---|---|---|---|
| 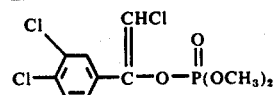 (known) | (B) | 0.1 | 0 |
| 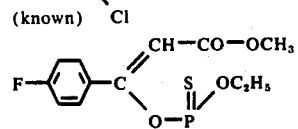 | (15) | 0.1 | 100 |
| 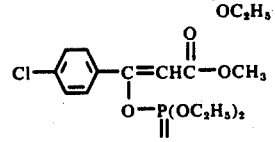 | (18) | 0.1 | 100 |
| 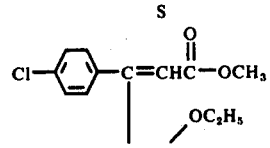 | (19) | 0.1 | 100 |
| 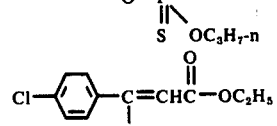 | (23) | 0.1 | 100 |
| 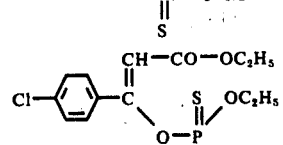 | (22) | 0.1 | 100 |
| 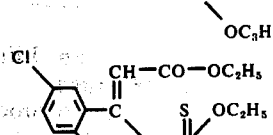 | (17) | 0.1 | 100 |

Table 6-continued (Myzus test)

| Active compound | | Active compound concentration in % | Degree of destruction in % after 1 day |
|---|---|---|---|
| [structure: 2,4-dichlorophenyl C=CHC(O)OC₂H₅ with O-P(=S)(OC₂H₅)₂] | (20) | 0.1 | 100 |
| [structure: 2,4-dichlorophenyl C=CH-CO-OC₂H₅ with O-P(=S)(OC₂H₅)(OC₃H₇-n)] | (21) | 0.1 | 100 |
| [structure: 2,4,5-trichlorophenyl C=CH-CO-OC₂H₅ with O-P(=S)(OC₂H₅)(OC₂H₅)] | (16) | 0.1 | 100 |
| [structure: 2,4,5-trichlorophenyl C=CH-CO-OC₂H₅ with O-P(=S)(OC₂H₅)₂] | (13) | 0.1 | 100 |
| [structure: 4-bromophenyl C=CH-CO-OC₂H₅ with O-P(=S)(OC₂H₅)₂] | (26) | 0.1 | 100 |
| [structure: 4-iodophenyl C=CH-CO-OC₂H₅ with O-P(=S)(OC₂H₅)₂] | (26) | 0.1 | 100 |
| [structure: 4-methylphenyl C=CH-CO-OC₂H₅ with O-P(=S)(OC₂H₅)(OC₃H₇-n)] | (24) | 0.1 | 100 |
| [structure: 2,4-dimethylphenyl C=CH-CO-OC₂H₅ with O-P(=S)(OC₂H₅)₂] | (1) | 0.1 | 100 |
| [structure: 4-(CH₃S)phenyl C=CH-CO-OC₂H₅ with O-P(=S)(OC₂H₅)₂] | (14) | 0.1 | 100 |
| [structure: 4-methoxyphenyl C=CH-CO-OC₂H₅ with O-P(=S)(OC₂H₅)₂] | (2) | 0.1 | 100 |
| [structure: 4-methoxyphenyl C=CH-CO-OC₂H₅ with O-P(=S)(OC₂H₅)(OC₃H₇-n)] | (30) | 0.1 | 100 |

EXAMPLE 7

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*) were sprayed with the preparation of the active compound until dripping wet. These bean plants were heavily infested with the two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following table:

Table 7

| Active compound | (*Tetranychus* test/resistant) Active compound concentration in % | Degree of destruction in % after 2 days |
|---|---|---|
| (known) (B) | 0.1 | 0 |
| (known) (C) | 0.1 | 0 |
| (15) | 0.1 | 98 |
| (18) | 0.1 | 99 |
| (20) | 0.1 | 95 |

The process of the present invention is illustrated by the following preparative Examples.

EXAMPLE 8 a. The benzoylacetic acid alkyl ester derivatives listed below and required as starting materials were prepared according to known processes described in the literature e.g. German published specification DOS No. 2,343,974.

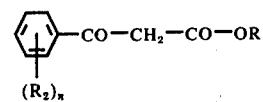

(VI)

| Intermediate | R | $(R_2)_n$ | Physical data (boiling point, °C/mm Hg; melting point, °C) | Yield (% of theory) |
|---|---|---|---|---|
| a | $C_2H_5$ | H | 115–120/1.5 | 87 |
| b | $C_2H_5$ | 4-OCH$_3$ | 170–178/1.0 | 85 |
| c | $C_2H_5$ | 4-CN | 140/0.1 | 84 |
| d | CH$_3$ | 4-Cl | 113/0.3 | 87 |
| e | $C_2H_5$ | 4-Cl | 125/0.1 | 86 |
| f | $C_2H_5$ | 4-C$_2$H$_5$ | 82 | 87 |
| g | CH$_3$ | 4-F | 115/0.05 | 52 |
| h | $C_2H_5$ | 4-I | 180/0.5 | 32 |
| i | $C_2H_5$ | 4-Br | 165/0.2 | 58 |
| j | $C_2H_5$ | 4-SCH$_3$ | 173/0.1 | 51 |
| k | $C_2H_5$ | 4-CH$_3$ | 148/1.0 | 76 |
| l | $C_2H_5$ | 2,5-Cl | 149/0.1 | 28 |
| m | $C_2H_5$ | 2,4-Cl | 155–165/0.3 | 30 |
| n | $C_2H_5$ | 2,5-CH$_3$ | 122–125/0.05 | 76 |
| o | $C_2H_5$ | 2,4-CH$_3$ | 130/0.05 | 74 |
| p | $C_2H_5$ | 2,4,5-Cl | 180–190/0.5 | 32 |
| q | $C_2H_5$ | 2,3,4-Cl | 160–170/0.1 | 10 |
| r | CH$_3$ | 2,4,6-Cl | 134/0.05 | 42.5 | b. The α-benzoylpropionic acid esters in question were obtained by methylating the sodium salts of the corresponding benzoylacetic acid ester derivatives in accordance with processes known from the literature.

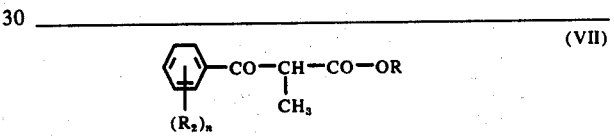

(VII)

| Intermediate | R | $(R_2)_n$ | Physical data (boiling point, °C/mm Hg; melting point, °C) | Yield (% of theory) |
|---|---|---|---|---|
| a | $C_2H_5$ | H | 114/0.1 | 83 |
| b | $C_2H_5$ | 4-Cl | 118–120/0.1 | 75 |
| c | CH$_3$ | 4-C$_6$H$_5$ | 195/0.05; 69 | 80 |
| d | $C_2H_5$ | 4-OCH$_3$ | 143–144/0.6 | 86 |
| e | $C_2H_5$ | 4-CN | 146/0.6 | 63 |
| f | $C_2H_5$ | 2,4-CH$_3$ | 125/0.05 | 52 |
| g | $C_2H_5$ | 2,5-CH$_3$ | 122/0.05 | 52 | c)

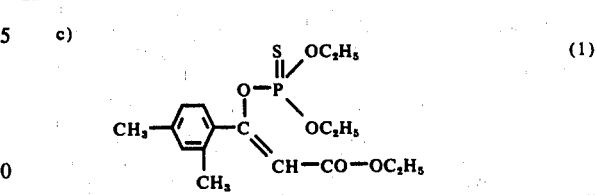

(1)

18.8 g (0.1 mole) of O,O-diethyl-thionophosphoric acid diester chloride were added dropwise, without cooling, to a mixture of 22 g (0.1 mole) of 2,4-dimethylbenzoylacetic acid ethyl ester, 12.3 g (0.11 mole) of potassium tert.-butylate and 250 ml of acetonitrile, and the reaction mixture was warmed to 60° C and stirred for a further 3 hours at this temperature. After cooling to room temperature, 400 ml of toluene were added. The batch was then extracted 3 times by shaking with 200 ml of water at a time, the toluene solution was dried over sodium sulfate and the solvent was distilled off under reduced pressure. The residue is subjected to "slight distillation". This gave 31.3 g (88% of theory) of O,O-diethyl-O-[1-(2,4-dimethylphenyl)-2-carbethoxyvinyl]-thionophosphoric acid ester in the form of a brown oil of refractive index $n_{25}^D$: 1.5218.

The following compounds of the formula

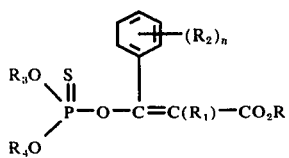

could be prepared analogously:

| Compound No. | $R_1$ | $(R_2)_n$ | $R_3$ | $R_4$ | Yield (% of theory) | Physical data (refractive index) |
|---|---|---|---|---|---|---|
| 2 | $C_2H_5-$ | H | 4-$OCH_3$ | $-C_2H_5$ | $-C_2H_5$ | 54 | $n_D^{24}$ : 1.5350 |
| 3 | $C_2H_5-$ | H | 4-$OCH_3$ | $-C_3H_7$-n | $-C_3H_7$-n | 55 | $n_D^{24}$ : 1.5317 |
| 4 | $CH_3-$ | $CH_3$ | 4-CN | $-C_2H_5$ | $-C_2H_5$ | 68 | $n_D^{23}$ : 1.5380 |
| 5 | $CH_3-$ | $CH_3$ | 4-$C_6H_5$ | $-C_2H_5$ | $-C_2H_5$ | 76 | $n_D^{20}$ : 1.5825 |
| 6 | $CH_3-$ | $CH_3$ | 4-Cl | $-C_2H_5$ | $-C_2H_5$ | 67 | $n_D^{23}$ : 1.5345 |
| 7 | $C_2H_5-$ | $CH_3$ | 4-$OCH_3$ | $-C_2H_5$ | $-C_2H_5$ | 77 | $n_D^{24}$ : 1.5300 |
| 8 | $CH_3-$ | $CH_3$ | 4-CN | $-C_2H_5$ | $-C_3H_7$-n | 50 | $n_D^{24}$ : 1.5445 |
| 9 | $CH_3-$ | $CH_3$ | 4-Cl | $-C_2H_5$ | $-C_3H_7$-n | 66 | $n_D^{24}$ : 1.5355 |
| 10 | $C_2H_5-$ | $CH_3$ | 4-$OCH_3$ | $-C_2H_5$ | $-C_3H_7$-n | 52 | $n_D^{23}$ : 1.5315 |
| 11 | $CH_3-$ | $CH_3$ | | $-CH_3$ | $-C_3H_7$-n | 58 | $n_D^{23}$ : 1.5841 |
| 12 | $CH_3-$ | $CH_3$ | 4-$C_6H_5$ | $-C_3H_5$ | $-C_3H_7$-n | 46 | $n_D^{23}$ : 1.5841 |
| 13 | $C_2H_5-$ | H | 2,4,5-Cl | $-C_2H_5$ | $-C_2H_5$ | 56 | $n_D^{24}$ : 1.5463 |
| 14 | $C_2H_5-$ | H | 4-$SCH_3$ | $-C_2H_5$ | $-C_2H_5$ | 70 | $n_D^{24}$ : 1.5800 |
| 15 | $CH_3-$ | H | 4-F | $-C_2H_5$ | $-C_2H_5$ | 48 | $n_D^{24}$ : 1.5224 |
| 16 | $C_2H_5-$ | H | 2,4,6-Cl | $-C_2H_5$ | $-C_2H_5$ | 81 | $n_D^{25}$ : 1.5404 |
| 17 | $C_2H_5-$ | H | 2,5-Cl | $-C_2H_5$ | $-C_2H_5$ | 77 | $n_D^{23}$ : 1.5351 |
| 18 | $CH_3-$ | H | 4-Cl | $-C_2H_5$ | $-C_2H_5$ | 83 | $n_D^{22}$ : 1.5338 |
| 19 | $CH_3-$ | H | 4-Cl | $-C_2H_5$ | $-C_3H_7$-n | 71 | $n_D^{22}$ : 1.5275 |
| 20 | $C_2H_5-$ | H | 2,4-Cl | $-C_2H_5$ | $-C_2H_5$ | 75 | $n_D^{26}$ : 1.5321 |
| 21 | $C_2H_5-$ | H | 2,4-Cl | $-C_2H_5$ | $-C_3H_7$-n | 65 | $n_D^{26}$ : 1.5311 |
| 22 | $C_2H_5-$ | H | 4-Cl | $-C_2H_5$ | $-C_3H_7$-n | 55 | $n_D^{23}$ : 1.5285 |
| 23 | $C_2H_5-$ | H | 4-Cl | $-C_2H_5$ | $-C_2H_5$ | 60 | $n_D^{23}$ : 1.5374 |
| 24 | $-C_2H_5-$ | H | 4-$CH_3$ | $-C_2H_5$ | $-C_3H_7$-n | 75 | $n_D^{26}$ : 1.5447 |
| 25 | $C_2H_5-$ | H | 2,5-$CH_3$ | $-C_2H_5$ | $-C_2H_5$ | 93 | $n_D^{25}$ : 1.5363 |
| 26 | $C_2H_5-$ | H | 4-Br | $-C_2H_5$ | $-C_2H_5$ | 93 | $n_D^{25}$ : 1.5493 |
| 27 | $C_2H_5-$ | H | 2,5-$CH_3$ | $-CH_3$ | $-CH_3$ | 79 | $n_D^{23}$ : 1.5283 |
| 28 | $C_2H_5-$ | H | 4-I | $-C_2H_5$ | $-C_2H_5$ | 98 | $n_D^{25}$ : 1.5441 |
| 29 | $C_2H_5-$ | H | 4-I | $-CH_3$ | $-CH_3$ | 81 | $n_D^{20}$ : 1.5832 |

Other compounds which can be similarly prepared include:

| Compound No. | R | $R_1$ | $(R_2)_n$ | $R_3$ | $R_4$ |
|---|---|---|---|---|---|
| 30 | $C_3H_7$-n— | H | 2,4,5-Cl | $-C_2H_5$ | $-C_3H_7$-iso |
| 31 | $C_4H_9$-iso- | H | 4-$OC_2H_5$ | $-CH_3$ | $-C_4H_9$-iso |
| 32 | $C_2H_5-$ | H | 4-$C_2H_5$ | $-C_2H_5$ | $-C_2H_5$ |
| 33 | $C_2H_5-$ | H | 4-$SC_2H_5$ | $-C_2H_5$ | $-C_2H_5$ |
| 34 | $C_2H_5-$ | H | 2-Cl,4-$CH_3$ | $-C_2H_5$ | $-C_2H_5$ | and the like.

It will be appreciated that the instant specification and examples are set forth by way of illustration and not limitation, and that various modifications and changes may be made without departing from the spirit and scope of the present invention.

What is claimed is:

1. An O,O-dialkyl-O-(1-phenyl-2-carbalkoxyvinyl)-thionophosphoric acid ester of the formula

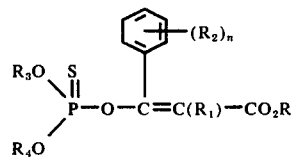

in which

R, $R_3$ and $R_4$, each independently is alkyl with 1 to 6 carbon atoms, $R_1$ is hydrogen or methyl, $R_2$ is alkyl, alkoxy or alkylthio each with 1 to 4 carbon atoms, cyano, halogen or phenyl, and n is 1, 2, 3, 4 or 5.

2. A compound according to claim 1, in which $R_3$ and $R_4$ each independently is alkyl with 1 to 4 carbon atoms, R is alkyl with 1 to 3 carbon atoms, $R_2$ is cyano, phenyl, chlorine, fluorine, bromine, iodine, methoxy, ethoxy, methylthio, ethylthio, methyl or ethyl, and n is 1, 2 or 3.

3. The compound according to claim 1, wherein such compound is O,O-diethyl-O- [1-(2,4,5-trichlorophenyl)-2-carbethoxyvinyl] -thionophosphoric acid ester of the formula

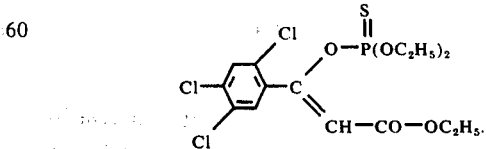

4. The compound according to claim 1, wherein such compound is O,O-diethyl-O- [1-(4-fluorophenyl)-2-carbmethoxyvinyl] -thionophosphoric acid ester of the formula

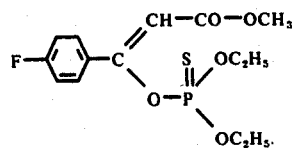

5. The compound according to claim 1, wherein such compound is O,O-diethyl-O- [1-(2,5-dichlorophenyl)-2-carbethoxyvinyl] -thionophosphoric acid ester of the formula

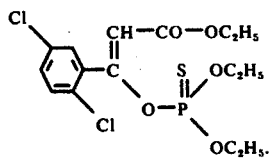

6. The compound according to claim 1, wherein such compound is O,O-diethyl-O- [1-(4-chlorophenyl)-2-carbmethoxyvinyl] -thionophosphoric acid ester of the formula

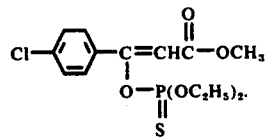

7. The compound according to claim 1, wherein such compound is O-ethyl-O-n-propyl-O- [1-(4-chlorophenyl)-2-carbmethoxy-vinyl] -thionophosphoric acid ester of the formula

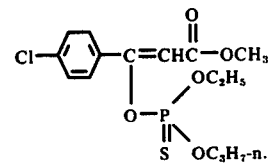

8. An insecticidal or acaricidal composition containing as active ingredient an insecticidally or acaricidally effective amount of a compound according to claim 1 in admixture with a diluent.

9. A method of combating insects or acarids which comprises applying to the insects or acarids, or to a habitat thereof, an insecticidally or acaricidally effective amount of a compound according to claim 1.

10. The method according to claim 9 in which said compound is

O,O-diethyl-O- [1-(2,4,5-trichlorophenyl)-2-carbethoxy-vinyl] -thionophosphoric acid ester, O,O-diethyl-O- [1-(4-fluorophenyl)-2-carbmethoxyvinyl] -thionophosphoric acid ester, O,O-diethyl-O- [1-(2,5-dichlorophenyl)-2-carbethoxyvinyl] -thionophosphoric acid ester, O,O-diethyl-O- [1-(4-chlorophenyl)-2-carbmethoxyvinyl] -thionophosphoric acid ester, or O-ethyl-O-n-propyl-O- [1-(4-chlorophenyl)-2-carbmethoxy-vinyl] -thionophosphoric acid ester.

* * * * *